United States Patent [19]

Goodman

[11] Patent Number: 5,162,303
[45] Date of Patent: Nov. 10, 1992

US005162303A

[54] PHARMACEUTICAL COMPOSITIONS CONTAINING PROLACTIN AND METHODS FOR THE USE THEREOF

[75] Inventor: Geoffrey Goodman, Kibbutz Amiad, Israel

[73] Assignee: Amiad Research and Development, Kibbutz Amiad, Israel

[21] Appl. No.: 592,964

[22] Filed: Oct. 4, 1990

[30] Foreign Application Priority Data

Oct. 8, 1989 [IL] Israel .......................................... 91928

[51] Int. Cl.⁵ ...................... A61K 37/00; A61K 31/34
[52] U.S. Cl. .......................................... 514/2; 514/474
[58] Field of Search ............................ 514/474, 2, 21

[56] References Cited

U.S. PATENT DOCUMENTS 3,887,705  6/1975  Serre et al. ........................... 424/180
4,668,516  5/1987  Duraffourd et al. .............. 424/196.1
4,695,452  9/1987  Gannis et al. .......................... 424/59
4,882,359 11/1989  Nakagawa et al. .................. 514/947
4,954,298  9/1990  Yamamoto et al. ................. 514/800
4,959,358  9/1990  Carey et al. ........................... 514/946

FOREIGN PATENT DOCUMENTS 046409   2/1982  European Pat. Off. .
1144263  2/1963  Fed. Rep. of Germany .
014587   1/1982  Japan .
222078  12/1983  Japan .
207289   9/1987  Japan .

Primary Examiner—Frederick E. Waddell
Assistant Examiner—Raymond J. Henley, III
Attorney, Agent, or Firm—Darby & Darby

[57] ABSTRACT

The invention provides a pharmaceutical composition for increasing the tensile strength of connective tissue while modifying the amount of cross-linked collagen therein comprising prolactin in an amount effective to increase the tensile strength of connective tissue as active ingredient therein in combination with a pharmacologically acceptable carrier.

15 Claims, No Drawings

PHARMACEUTICAL COMPOSITIONS CONTAINING PROLACTIN AND METHODS FOR THE USE THEREOF

The present invention relates to a pharmaceutical composition for increasing the tensile strength of connective tissue while modifying the amount and nature of cross-linked collagen therein.

More particularly the present invention relates to a composition comprising the pituitary peptide hormone (prolactin, PRL) alone and in combination with ascorbic acid, (Vitamin C) or with an ascorbate in order to enhance the appearance of and restore and preserve skin and to maintain and restore the performance of physiological structures in which connective tissue and its constituents play a major role.

The mechanical characteristics (e.g. tensile strength, elasticity, turgor) of the various tissues of the body are usually provided by an extra-cellular matrix. This consists of a complex, organized network of inter-acting protein and polysaccharide macromolecules, which are secreted by cells dispersed within the matrix. The term, connective tissue, usually denotes the matrix together with the cells embedded or migrating within it. Connective tissue is particularly evident in the skin, skeletal, cardiovascular and gut systems. It may be highly specialized (e.g. in tendons) or provide a general physical stability, as in most tissues and organs (e.g. skin, arterial wall).

Because of their abundance (25% of all protein in mammals; 75% of skin protein), the contribution of the fibrous proteins, known as collagens, to connective tissue function has been much emphasized. However, despite intensive study and increasingly detailed knowledge of the structure of the collagens, there is a relative lack of knowledge of some other major connective tissue components and only a very fragmentary understanding of the overall organization of the latter, a situation which may have led to some precipitate and possibly even erroneous conclusions.

Thus, even a relatively recent disclosure (U.S. Pat. No. 4,668,516), stated: "Collagen consists of long elastic polypeptide fibres interconnected by bridges which provide the cohesion and stability of the connective tissue. This texture enables it to act as an elastic tissue in every direction and retain water, thus actively taking part in water control at the skin. Collagen aging manifests itself as a break in the connections between the fibres. Age, severe weather, and pollution accelerate these breaks and slow down their renewal. Accordingly, the skin loses its elasticity and dehydrates." The factual accuracy of most of the latter is questionable.

Although more reliable information exists about the role of collagen in connective tissue and particularly in skin, much is unknown. For example, no reliable quantitative data have been published correlating wrinkling of skin with measurable parameters, collagenous or other. Uncertainty is added by the fact that collagen metabolism is a dynamic process in connective tissues, synthesis and degradation usually proceeding in parallel, the ratio between them varying with circumstances.

Collagen polypeptide chains (seven variants are known) are combined into triple-stranded stiff, non-elastic, helical molecules. Because of the variant chains, composition of the helices may differ, though few variations are known. The major ones are collagen types I, II, III, IV and V. Type I is widespread, including in skin, II is common in cartilage and III in skin and blood vessels. The significance of these specializations for connective tissue architecture and function is unknown. After secretion, collagen molecules of types I–III polymerise into micro fibrils, which then bind into fibrils, with varying degrees of intra and inter-molecular covalent crosslinking. The fibrils are often bunched into fibres. The arrangement in tissues of types IV and V is unknown.

As tissue matures, the number of reducible collagen crosslinks declines, due to their conversion to non reducible crosslinks. Till now, this has been thought to be the cause of increasing skin tensile strength with time, a view related to past evidence that skin tensile properties appear to mainly depend on collagen. However, like so much else in the field of connective tissue physiology, the nature of the mature collagen crosslinks is uncertain and they differ in different collagen-rich tissues.

Collagenous fibres are never branched but are interwoven in a loose felt-type arrangement. Far from being elastic, they resist stretching and are embedded in a highly hydrated ground substance, formed from the polysaccharide glycosoaminoglycans (GAG's). Increasing attention is now being given to non-collagenous elements such as the latter, elastin and fibronectin, and to what may be more critical than any of the above separately, namely, the interrelationships between them, and between them and the cyto-skeletons of the matricial cells.

GAG's are usually large, highly extended, randomly-coiled and highly hydrophilic proteoglycans i.e. GAG's covalently linked to a protein core. The GAG's and other macromolecules influence formation of collagen fibrils and bind to them, sometimes in a highly regular pattern, creating three-dimensional structures, the details and functions of which are unknown.

A randomly-coiled, highly cross-linked protein, elastin, once thought to be degenerate collagen, is now recognized as an important contributor to mechanical characteristics of connective tissues, particularly elasticity. In contrast to collagen, the elastin-based fibres are branched and therefore form true networks. The matrix also contains glycoproteins and one at least, fibronectin, is recognized as a major promoter of cell-cell and cell-collagen adhesion. Others no doubt, are as yet undetected.

It is thought that the architecture of the extracellular matrix is also partly determined by the orientation of the cytoskeleton of the cells which secrete the macromolecules into the extra-cellular space. It is not known whether this contributes to the tensile and other mechanical characteristics of connective tissue.

From the above, it seems that structurally the matrix is not merely a bed for collagen, even though by weight, the latter may dominate in some tissues. Many interactions between the components of connective tissue and between them and the cells with which they are in contact, remain to be elucidated.

Many humoral substances are known to influence one or more of the constituents of connective tissue. One of these is prolactin (PRL), a pituitary peptide traditionally associated with formation of tissues providing nutrition for the young (mammary glands; pigeon "milk"). Additional cell-proliferative and developmental effects of prolactin are known, particularly in some classes of the lower vertebrates.

Thus, in tadpoles, bovine PRL stimulated the growth of connective tissue both in the fins and other regions of the tail (Yoshizato K. and I. Yasumasu (1970) Effect of prolactin on the tadpole fail fin.-I. Stimulatory effect of prolactin on the collagen synthesis of the tadpole tail fin. Development, Growth and Differentiation 2:305–317). Collagen content was specifically enhanced about forty-fold due to enhanced synthesis. PRL also stimulated the incorporation of precursors into hyaluronic acid (a GAG) in tadpoles and inhibited hyaluronidase activity. (Yoshizato K. and I. Yasumasu (1972) Effect of prolactin on the tadpole tail fin.-IV. Stimulatory effect of prolactin on the metabolic fate of hyaluronic acid collagen and RNA with special reference to catabolic process. Development, Growth and Differentiation 14:119–127).

A number of effects of PRL on the skin of reptiles and their appendages are known. It may act directly on lizard skin, as it caused sloughing in the absence of pituitary and thyroid glands (Chiu K. W. and J. G. Phillips (1971) The effect of prolactin on the sloughing cycle of the hypophysectomized-thyroidectomized lizard, Gecko gecko L. J. Endocrinol. 49:619–624), and has specific mitogenic effects on the mammary gland which is derived from the skin, In the newt, hypophysectomy reduces proliferation of the stratum germinativum to a very low level (Hoffman C. W. and J. N. Dent (1973) Stimulation of mitotis by prolactin in the epidermis of the red-spotted newt. Amer. Zool. 13:1281 (Abst.)). This is restored by exogenous PRL, which is stimulatory in unoperated animals. In the tadpole, PRL stimulated proliferation of basal epidermal cells of the tail fin (Wright M. L., M. A. Majeowski, S. M. Lucas and P. A. Pike (1979) Effect of prolactin on growth, development and epidermal cell proliferation in the hindlimb of the Rana pipiens tadpole. Gen. Comp. Physiol. 39:53–62). Nuptial pads, cornified structures serving courtship manoeuvres are found in some classes of lower vertebrates (Singhas C. A. and J. N. Dent (1975) Hormonal control of the tail fin and of the nuptial pads in the male red-spotted newt. Gen. Comp. Endocrinol. 26:382–393). In some of the species concerned, PRL is required for their development, though not solely. In many bird species, brood patches are formed (Bailey R. E. (1952) The incubation patch of passerine birds. Condor 54:121–136). Feathers fall from the breast and the bared skin becomes thick and hypervascularized. In some species PRL is required, though not alone; in others, patch formation is initiated by steroids and augumented by PRL (Jones R. E. (1971) The incubation patches of birds. Biol. Rev. 46:315–339).

In contrast to and despite the non-mammalian research indicated above, heretofore no data has been available on the effect of the hormone on the tensile strength of mammalian skin and no proposal has been made for using endogenous PRL to influence the constitution and functional characteristics of connective tissue in the repair of skin traumas and pathological states. It seems that there are no published data concerned with, or suggestion for utilizing PRL generally to effect structure and function of connective tissue in other physiological systems, e.g. vessel walls throughout the cardiovascular system. The state of the art described above may at least partly be due to a conservative and somewhat exclusive emphasis on lactational and reproductive functions of PRL.

It has been found now that systemic treatment with PRL greatly increases the tensile strength of the skin of the nude rat, while reducing the total number of collagen crosslinks and the ratio of non-reducible (mature) cross-links to reducible cross-links. The collagen data signifies a reduction or slowing in maturation, a novel finding considering the prior teaching that collagen maturation increases tensile strength of skin. The increased skin strength was also obtained despite a reduction in the amount of collagen found per gram of skin tissue.

Thus, according to the present invention there is now provided a pharmaceutical composition for increasing the tensile strength of connective tissue while modifying the amount and nature of cross-linked collagen therein comprising prolactin in an amount effective to increase the tensile strength of connective tissue as active ingredient therein in combination with a pharmacologically acceptable carrier.

In one aspect of the present invention there is provided a topical composition according to claim 1 for protecting and restoring connective skin, tissue comprising prolactin in an amount effective to increase the tensile strength of skin while reducing the amount and modifying the nature of collagen cross-links in the skin, as active ingredient therein.

In another aspect of the present invention there is provided a pharmaceutical composition according to claim 1 wherein said active ingredient and carrier are formulated for internal admistration.

In Israel specification filed concurrently herewith there are described and claimed pharmaceutical compositions for increasing the tensile strength of connective tissue while reducing the amount of cross-linked collagen therein comprising ascorbic acid (AA) or an ascorbate useful in medicaments as active ingredient therein which does not form a part of the present invention.

The role of AA in collagen metabolism may be contradictory e.g. the results of marginal deficiency of AA and a severe shortage may be opposite. Also, in grossly scorbutic guinea pigs, tensile strength of healing wounds significantly differed from that in normal controls on the eighth and tenth day after operation but not on the fourth and sixth days. It seemed reasonable that such apparent inconsistencies in the complex AA-collagen relationship could be at least partly due to interactions of AA with other humoral factors, such as PRL.

Over a physiological range, AA stimulates the conversion of free dihomogammalinoleic acid (DGLA) to prostaglandins, particularly PGE1, in human platelets. Prostaglandins have a role in connective tissues, e.g. in cats, hair loss and problems caused by essential fatty acid deficiency can be treated by the PG1 series alone. PGE1 seems to regulate formation of the glycosaminoglycans. As DGLA is released from its stored esterified form in membranes by, amongst others, PRL, an inter-action between AA and PRL may supplement the independent roles played by each in connective tissue.

Thus, in another aspect of the present invention there is provided a pharmaceutical composition comprising a combination of prolactin and ascorbic acid or prolactin and an ascorbate as combined active ingredients therein.

Ascorbates other than ascorbic acid which come into consideration are all those ascorbates useful in medicaments including magnesium ascorbate, sodium ascorbate and ascorbyl palmitate.

In experiments carried out in accordance with the present invention substantial differences were found between the effect of PRL alone and when administered together with AA. The skin from both back and stomach of rats receiving PRL and AA jointly was stronger, highly significantly so, than that of untreated rats, and the dorsal skin of rats treated with PRL and AA was stronger, highly significantly so, than that of rats treated with PRL alone, which skin as mentioned was itself much stronger than that of untreated rats. However, contrary to the unexpected results of treatment with PRL alone, the joint treatment caused an increase in insoluble collagen, parallel to the great increase in skin strength.

Clearly, the interaction of PRL with AA in rats involves some connective tissue mechanisms different from and additional to those operating when PRL is administered alone, suggesting the possibility of tailoring treatments for a range of therapeutic, preservative and cosmetic needs.

Understanding of those aspects of the current invention which relate to tissue repair requires consideration of the nature of scar tissue, compared to regenerated tissue. In lower vertebrates, true regeneration occurs e.g. in replacement of amputated lizard tails. In higher vertebrates, particularly mammals, wound repairs results in a fibrous, collagenous scar replacing the destroyed tissue. A similar tendency exists following destruction of tissue by disease. The scar may cause physical and functional aberrations, with sometimes drastic consequences. Scar synthesis is not the most desirable solution for tissue repair.

Normal skin collagen is different from dermal scar collagen. The latter contains more Type III collagen which has a higher rate of fibrillogenesis. A high proportion of Type-III collagen is found in hypertrophic scars. The possibility of varying the ratios of different types of collagen present is important when seeking an improvement in wound healing and in the repair and maintenance of all physical systems in which the quality of connective tissue is affected by injury, disease or aging.

Another unexpected discovery was a remarkable reduction in the proportion of Type-III collagen present in the skin of nude rats treated with PRL alone. In view of the above, this finding implies that PRL treatment of wounds can introduce into the healing process an element of tissue regeneration, resulting in superior healed tissue and the possibility of avoiding scar hypertrophy. However, here too, when the PRL was administered together with AA. the proportion of Type-III collagen was very different to that from the rats treated with PRL alone, indeed it was double that in untreated rats.

The present invention provides a novel method and composition whereby administration of appropriate amounts of PRL increases the tensile strength of skin while reducing or delaying maturation of said skin by decreasing the total number of collagen cross links and the proportion of non-reducible cross-links and while reducing the amount of Type III collagen present.

Furthermore, there is now provided a novel method and composition whereby administration of appropriate amounts of prolactin together with appropriate amounts of ascorbic acid increases the tensile strength of skin without reducing or delaying maturation of said skin whilst at the same time increasing the amount of Type-III collagen present.

Another embodiment of the invention provides a novel method comprising administration of appropriate amounts of PRL in a composition with one or more other factors, in suitable carrier. The said factor or factors, such as somatotrophin (Growth Hormone) and somatomedins and Epidermal Growth Factor by non limiting example, can be ones with known somatotrophic effects and can also be vitamins such as Vitamin A and Vitamin E, by non-limiting example. However, to remove all possible doubt, the said PRL-containing composition may include any factor or factors, natural and synthetic, beneficial and not harmful to the purposes herein declared.

The invention also provides a method whereby treatment with prolactin hastens the healing of wounds as judged by their tensile strength and modifies the content of Type III collagen in the scar tissue formed during said healing.

The invention also provides a method whereby treatment with prolactin jointly with ascorbic acid hastens the healing of wounds substantially beyond that obtained by each of the said ingredients alone.

In another aspect of the invention, the skin may be treated with PRL, as the sole active ingredient in a suitable medium, by topical or systemic methods in order to restore, maintain and improve the aesthetic appearance of skin.

In a further aspect of the invention, the skin may be treated with PRL in a composition together with one or more other active factors in suitable carrier by topical or systemic means, in order to restore, maintain and improve the aesthetic appearance of skin. The said PRL-containing composition may include any factor or factors, natural and synthetic, beneficial and not harmful to the cosmetic purposes herein declared.

Said PRL can be ovine prolactin, human prolactin or any other suitable prolactin from natural source or prolactin obtained by genetic engineering technology or analogues or derivatives of said prolactins.

Said administration can be by appropriate known systemic and topical routes such as intramuscular or sub cutaneous injection and external application, periodic or continuous by means such as a patch. Administration of PRL jointly with another factor can also be carried out by different routes for each ingredient.

The carrier used in formulating compositions of the present invention can be any suitable toxicologically and veterinarally acceptable carrier known per se and it can include suitable chemical means for increasing the degree or rate of absorption by tissues.

Compositions according to the present invention will comprise the active ingredients disclosed herein and will be presented for use in any conventional manner in admixture with one or more physiologically acceptable carriers or excipients. Thus, the active ingredients of the present invention may be formulated for oral, buccal, parenteral, topical or rectal administration.

The compositions may also be formulated for injection or for infusion and may be presented in unit dose form in ampules or in multi-dose containers with an added preservative.

The compositions may take such forms as suspension, solutions, or emulsions in oily or aqueous vehicles, and may contain formulatory agents such as suspending, stabilizing and/or dispersing agents. Alternatively, the active ingredients may be in powder form for constitution with a suitable vehicle, e.g. sterile, pyrogen-free water, free water, before use.

The pharmaceutical compositions according to the invention may also contain other active ingredients such as antimicrobial agents, or preservatives.

The preferred range of daily doses of prolactin active ingredient for systemic treatment will be about 15–50 i.u./lkg BW in saline solution and for topical treatment will be about 0.05-1.0 i.u. in 0.2 gr cream. The preferred range of daily doses of ascorbic acid when used in combination with prolactin for systemic treatment will be about 4-20 mg/lkg BW in saline solution and for topical treatment will be about 0.0066-0.132 mg in 0.2 gr cream.

Methods and formulations disclosed herein are believed to be valuable for:

a) clinical, veterinary and cosmeto-dermatological purposes, the latter purpose in particular rapidly increasing in importance, due to rising living standard, b) a population with a rising average age and need for protection from and treatment for the pathologies of aging, that of skin being the most obvious but not the most critical case.

c) meeting public preference for use of natural rather than artificial agents in drugs and cosmetics, d) obtaining vertebrate animal skins with physical characteristics varied to meet the requirements of industries producing leather goods.

While the invention will now be described in connection with certain preferred embodiments in the following examples so that aspects thereof may be more fully understood and appreciated, it is not intended to limit the invention to these particular embodiments. On the contrary, it is intended to cover all alternatives. modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

PREPARATIVE EXAMPLE 1

Ovine Prolactin was obtained from Sigma, U.S.A. and dissolved in alkaline saline medium which was returned to physiological pH with 0.1N HCl. The concentration of PR1 was such that the rats received 25 i.u./kg BW daily in 0.1 ml medium. Fresh solution was prepared every four days.

PREPARATIVE EXAMPLE 2

Sodium Ascorbate in buffered physiological saline was obtained from Teva (Israel) in a dilution so that the daily dose (4 mg) would be provided in a volume of 0.1 ml of medium.

BIOLOGICAL EXAMPLE 3

Twenty-four nude male rats (IFFA-CREDO, France>) were divided into four equal groups of equal average weight (280 gr): two control groups and two treatment groups (Table 1). The animals were weighed weekly. At time zero, after a period of adaptation, one of the control groups was sacrificed and full thickness skin samples were taken from the dorsum and underbelly for immediate testing and examination. The two treatment groups (PRL and PRLAA) were injected daily (ip), 6 days per week. for four weeks. PRL group received PRL solution only and the PRLAA group received both the PRL and AA solutions. The remaining control grup received physiological saline. Both groups were then weighed and sacrificed. Skin samples were taken as previously. Using equipment specially designed for the purpose, the tensile strength of standard widths of skin was measured by applying an increasing weight (grams) strain, to breaking point. Group means were analyzed using the Cochran unpaired two tailed t-test.

Coded samples of skin were removed for biochemical studies, which were carried out in triplicated assays. The samples were pooled per group, weighed and subjected to differential salt, acid and pepsin extraction used 1.0M NaCl (buffered with 0.05M tris, pH 7.6), 0.05M acetic acid and pepsin (0.005 g/ml), respectively, to obtain the relative amounts of neutral, salt, acid and pepsin-soluble collagen fractions present. The amount of collagen in each fraction was determined by its hydroxyproline contents following acid hydrolysis. Samples of each fraction were further thermally denatured and the separate alpha-, beta- and gamma-fragments, i.e. monomers, dimers and trimers respectively, were subjected to electrophoresis on poly-acrilimide gel slabs using the interrupted reduction method. This enabled the determination of the relative presence of cross-links in the different samples, as well as the presence of different types of collagen, such as Type-III, etc.

The PRL treatment caused an increase of 29% and 52% respectively in the tensile strength of dorsal ($p<0.008$) and ventral ($p<0.002$) skin (Table 1) and the PRLAA treatment caused an increase of 87% and 68% respectively in the tensile strength of dorsal ($p<0.0004$) and ventral ($p<0.0005$) skin of young nude male rats. Dorsal skin was significantly stronger than ventral skin in both groups.

TABLE 1

The effect of ovine prolactin (PRL) alone. or when administered together with ascorbic acid (PRLAA). on the tensile strength (gr) of dorsal and ventral skin from young nude rats.

| | Controls | | PRL | PRLAA |
|---|---|---|---|---|
| | Zero Time gr | Experimental gr | gr | gr |
| Dorsal | 560 +/− 39 | 2424 +/− 170 | 3127 +/− 159 | 4534 +/− 372 |
| Ventral | 387 +/− 32 | 909 +/− 88 | 1381 +/− 90 | 1525 +/− 87 |

+/− S.E.:
N = 6.

As there were no consistent differences between the dorsal and ventral samples, biochemical data for both have been averaged.

(a) Total collagen: insoluble and soluble collagen

The greatest amount of total collagen (per mg tissue) was found in the skin of the (younger) zero time control rats (Table 2). Total collagen in the PRL rats was lower than in all other groups whereas in the PRLAA group it was greater than in the experimental controls. The proportion of soluble collagen in skin of the PRLAA rats was much lower than in all other groups and that in PRL rats (more than half of the total collagen) much higher.

TABLE 2

The effect of ovine prolactin (PRL) alone, or when administered together with ascorbic acid (PRLAA), on the total and soluble collagen extracted from rat skin samples, as indicated by the absolute (ug/mg tissue) and relative (%) hydroxproline content of the extracts.

|  | Controls | | | |
| --- | --- | --- | --- | --- |
|  | Zero Time | Experimental | PRL | PRLAA |
| Total Collagen ug/mg | 3.44 | 2.42 | 2.00 | 2.95 |
| Soluble Collagen ug/mg | 1.29 | 0.76 | 1.10 | 0.40 |
| Soluble Collagen as % of Total | 37.5 | 31.4 | 55.0 | 13.6 |

N = 6.

(b) Total cross-links and % of Type-III collagen

Data are not available for zero-time control rats. In the PRL rats, the percentage of gamma (mature) Type I collagen (Table 3) was much lower (29.4%) than in the experimental Controls (49.2%) and in the PRLAA (45.2) group. Total percentage of crosslinked (beta- plus gamma-) collagen in PRL rats was also considerably less. Percentage of Type-III collagen in PRL rats was less than a third of that in the Control rats and one sixth of that in the PRLAA group.

TABLE 3

The effect of ovine prolactin (PRL) alone, or when administered together with ascorbic acid (PRLAA), on the distribution of alpha-beta- and gamma-bands of Type-I and of Type-III collagen (% of total) as demonstrated by electrophoretic separation of denatured and reduced collagen obtained by NaCl extraction from rat skin samples.

|  | Experimental Controls % | PRL % | PRLAA % |
| --- | --- | --- | --- |
| alpha-1 | 20.5 | 29.4 | 20.2 |
| alpha-2 | 13.4 | 14.5 | 7.3 |
| beta's | 10.8 | 24.8 | 15.3 |
| gamma's | 49.2 | 29.4 | 45.2 |
| Total x-links (beta + gamma) | 60.0 | 54.2 | 60.5 |
| Type-III | 6.5 | 2.0 | 12.7 |

N = 6

Administration of PRL caused a substantial and highly significant increase in the tensile strength of skin in the growing, nude rat. The biochemical studies show that this was not due to increase in total skin collagen, as estimated by the amount of hydroxyproline present per gram of tissue, or to increase in insoluble (mature) collagen. Nor was the increased strength caused by greater crosslinking of the collagen, which instead was reduced by the PRL treatment. Furthermore, if solubility of collagen is a measure of 'aging' of skin, then that treated with PRL was 50% 'younger' even than that in rats some weeks younger in time. This result in PRL rats is the very opposite of what was expected according to the accepted view that mechanical strength of skin is positively related to collagen maturation.

Equally interesting were the results of joint treatment with PRL and AA. The tensile strength of the dorsal skin of these rats was 50% greater than that of rats treated with PRL alone and almost double that of the experimental Controls. The effect of the double treatment on ventral skin was not so outstanding, when compared to that from treatment with PRL alone, but it was still very great, when compared to the experimental Controls. The reason for the differences between the two skin sites are not known. Unlike the results for PRL given alone, the tensile strength data from the PRLAA treatment were paralleled by greater maturity of collagen.

There is no consistent relationship between the levels of Type-III collagen in the skin samples from the different groups and their tensile strength. However, the great differences in Type-III levels under the different treatments may have a therapeutic outcome related to non-tensile characteristics of skin. Dermal scar tissue is not regenerated normal tissue. It contains a high proportion of Type-III collagen which is known to have a higher rate of fibrillogenesis than Type-I collagen. Hypertrophic scar tissue has an even higher level of Type-III. The findings here present a means to control some aspects of the nature of scar tissue and this will be particularly important when areas of the skin are involved (burns, disease) rather than incisions.

PREPARATIVE EXAMPLE 4

Ovine Prolactin (PRL) was obtained from Sigma, U.S.A. and dissolved in alkaline saline medium which was returned to physiological pH with 0.1 N HCl. The concentration of PRL was such that the rats received 16 i.u./kg BW daily in 0.1 ml medium. A fresh solution was prepared after three days.

PREPARATIVE EXAMPLE 5

Sodium Ascbrbate (AA) in buffered physiological saline was obtained from Teva (Israel) and diluted so that the daily dose (2 mg) would be provided in a volume of 0.1 ml of medium.

BIOLOGICAL SAMPLE 6

Male chickens (commercial crossed breed) aged 28 days and weighing an average of 1000 gr. were allocated randomly to three groups, those to be treated (groups PRL and PRLAA) and a control group (C). They were then distributed randomly two to a cage in an environmentally-controlled building ($25+/-1°$ C.). Feed and water were supplied ad lib. After an adaptation period and on the same day that treatment started, surgery was performed with use of a local anaesthetic. In each bird, a 15 mm long incision was made to the full depth of back skin on the right side close to the pelvis and 1.5 cms from the spine, using a standard scalpel bearing a No. 20 Swann-Morton surgical steel blade. The wound was sown with one central stitch, using standard surgical thread. No antiseptic treatment was applied to the wound, at any time.

Starting on the day of surgery, once daily at 07.00 hours, for seven days the birds were injected im in the thigh, either with saline alone (Controls), or with prolactin (PRL) or with both prolactin and ascorbic acid (PRLAA).

On sacrifice, two samples of back skin were removed, one including the wound site, the other being taken from the left side, at a contra-lateral position. Prior to removal of the 5×2 cm. samples, a pair of short (about 6 mm) incisions (5mm between them) were made across the wound site at an angle of 90 degrees. For this, two Swann-Morton scalpels (No. 3) were bound together tightly, along their flat sides with each bearing a No. 11 blade. The samples were stored at 4° C. and later, on the day of sacrifice, they were tested for tensile strength, as described above. The strength of the repairing wound in each bird, was compared with that of the unoperated skin sample from the same bird. Differences between group means were analyzed using Student's t-test.

The birds were healthy throughout. Final weights did not differ. Force needed to tear the wound scars is shown in Table 4.

TABLE 4

Absolute tensile strength of skin scars in young, male chickens after injections for seven days with PRL or PRLAA or saline, strength of the scars relative to strength of non-incised skin in the same birds (Internal Controls) and relative to strength of scars of Control birds (External Controls).

| | Scar Tensile Strength | Strength Relative to Controls | |
|---|---|---|---|
| | gr | Inner % | External % |
| PRL | 368 +/− 32 | −29 +/− 8 | +34 |
| PRLAA | 346 +/− 17 | −35 +/− 4 | +26 |
| Controls | 274 +/− 27 | −47 +/− 8 | — |

+/− S.E.;
N = 8

After 7 days treatment, scar tensile strength was significantly ($p<0.01$) greater in both treatment groups. There was no benefit from systemic addition of AA to the PRL treatment.

In earlier preliminary experiments, injections of PRL and AA separately, increased tensile strength of intact chicken skin. Here, injection with PRL but not with AA significantly increased the tensile strength of scars from skin incisions, seven days after surgery. The level of treatment with AA was lower in this Biological Example than in the said preliminary experiments and lower than in Biological Example 3 and the period of treatment was only a quarter of that in the latter. Also, endogenous production of AA may be rapidly reduced to balance systemic intake. The mechanism by which the known rapid concentration of systemic AA takes place at wound sites, may be saturated in the chicken, or require much higher levels of AA input to influence it positively, compared to rats; more favorable could be topical AA application to the wound site.

PREPARATIVE EXAMPLE 7

Ovine prolactin (Sigma, U.S.A.,) was dissolved in saline at physiological PH, as in Preparative Example 1. It was then added to a standard commercial moisturizing cream base in an amount ensuring wound treatment equal to that which would result from the systemic provision of 30 i.u. daily, assuming equal distribution of the latter throughout the body. The cream was mixed thoroughly and stored at 10° C.

PREPARATIVE EXAMPLE 8

Sodium Ascorbate solution buffered to physiological pH (Teva, Israel) was added to a standard comercial moisturizing cream base in an amount that would ensure wound treatment equal to that which would result from the systemic provision of 2 mg daily, assuming equal distribution of the latter throughout the body. The cream was mixed thoroughly and stored at 10° C.

BIOLOGICAL EXAMPLE 9

Young male chickens were allocated, housed and maintained and skin incisions were placed, as in Biological Example 6. One hour after surgery and then twice daily at 6:30 and 17:00 hours, for 7 days, 0.1 gr of cream prepared according to Preparative Example 7 and containing PRL was applied carefully to and gently around the incision site of the PRL and the PRLAA treatment groups, and also rubbed in gently around the site. This procedure was repeated for the PRLAA group, with 0.1 gr of cream containing AA prepared according to Preparative Example 8. Control birds received the base cream without PRL or AA.

On sacrifice, skin samples were taken and tested as described above. Group means were analyzed by Student's t-test.

The birds were healthy throughout. Final weights did not differ. Force needed to tear the wounds is shown in Table 5. The absolute increase in the PRL group compared to the Controls was much smaller than when the PRL was administered by injection in Biological Example 6, however, the increase was substantial as in the latter, when comparing the intact skin in the same bird.

TABLE 5

Absolute tensile strength of skin scars in three groups of young male chickens, strength of latter scars relative to strength of non-incised skin in the same birds (Internal Controls) and relative to strength of scars of Control birds, after treatment for seven days with a cream containing PRL (Group PRL) or with PRL and AA (PRLAA), or a cream containing neither PRL or AA (External Controls).

| | Scar Tensile Strength | Strength Relative to Controls | |
|---|---|---|---|
| | gr | Inner % | External % |
| PRL | 462 +/− 33 | −34 +/− 6 | +5 |
| PRLAA | 561 +/− 27 | −39 +/− 5 | +28 |
| Controls | 439 +/− 34 | −45 +/− 6 | — |

+/− S.E.;
N = 6

The absolute tensile strength of the scars in the PRLAA wounds was significantly stronger than in the control birds ($p<0.04$).

In this Example the topical application of AA, additional to topical application of PRL in the same birds, caused a considerable improvement in skin wound repair in animals which do not require dietary AA. Thus topical AA treatment in birds was more effective than systemic. The smaller effect of the PRL alone, in absolute terms, may have been fortuitous; it was more substantial when compared to internal control skin samples. However, these results may indicate that for PRL, injection is a superior route.

From the present invention it can be seen that in animals of a mammalian species, administration of PRL in an appropriate dose and manner and during an appropriate period can, contrary to the accepted concept, delay the maturation of collagen and at the same time increase skin tensile strength. Thus the treatment preserves what are generally regarded as some of the biochemical characteristics of young, immature skin, but not at the cost of mechanical strength.

It has further been shown that joining treatment with AA to that with PRL creates a synergistic effect, resulting in certain skin biochemical characteristics greatly different to those evident when the two materials are administered alone, while at the same time causing an increase in skin tensile strength, which is highly significantly greater than that of the increases obtained by the materials individually, when compared to appropriate control animals.

Additionally, whereas maturation of collagen usually increases tensile strength of skin, the present findings teach that such an increase is not necessarily directly dependent on collagen and that there exists an independent not primarily collagenous mechanism through which treatment with prolactin has an alternative and probably specific influence on the degree and nature of integration within the matricial architecture of connective tissue.

Furthermore it is taught here that prolactin alone and in co-treatment with AA can substantially vary the level of Type-III collagen present in connective tissue.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A pharmaceutical composition comprising an effective amount of prolactin; ascorbic acid or an ascorbate; and a pharmacologically acceptable carrier; wherein the amounts of prolactin and ascorbic acid or ascorbate are effective to modify the amount of Type III collagen in connective tissue.

2. A pharmaceutical composition according to claim 3 wherein the composition is in topical form.

3. A pharmaceutical composition according to claim 3 wherein said active ingredient and carrier are formulated for internal administration.

4. A pharmaceutical composition according to claim 3 wherein said connective tissue is connective tissue of the skeletal system.

5. A pharmaceutical composition according to claim 3 wherein said connective tissue is cardiovascular connective tissue.

6. A pharmaceutical composition according to claim 3 wherein said connective tissue is connective tissue of the gastrointestinal tract.

7. A pharmaceutical composition comprising an effective amount of prolactin; ascorbic acid or an ascorbate; and a pharmacologically acceptable carrier; wherein the amounts of prolactin and ascorbic acid or ascorbate are effective for promoting wound and tissue healing.

8. A pharmaceutical composition according to claim 7 wherein said active ingredient and carrier are formulated for internal administration.

9. A pharmaceutical composition according to claim 7 wherein said connective tissue is connective tissue of the gastrointestinal tract.

10. A pharmaceutical composition comprising an effective amount of a combination of prolactin and ascorbic acid or prolactin and an ascorbate as active ingredients therein, together with a pharmacologically acceptable carrier wherein the amounts of prolactin and ascorbic acid or ascorbate are effective to increase the tensile strength of connective tissue.

11. A pharmaceutical composition according to claim 17 wherein said active ingredient and carrier are formulated for internal administration.

12. A pharmaceutical composition according to claim 17 wherein said connective tissue is connective tissue of the gastrointestinal tract.

13. A method for protecting and restoring skin connective tissue in a mammalian or avian species comprising applying a topical cosmetic composition comprising prolactin in an amount effective to increase the tensile strength of connective tissue as active ingredient therein in combination with a pharmacologically acceptable carrier.

14. A method for protecting and restoring connective tissue in a mammalian or avian species comprising internally administering to said mammalian or avian species a pharmaceutical composition comprising prolactin in an amount effective to increase the tensile strength of connective tissue as active ingredient therein in combination with a pharmacologically acceptable carrier.

15. A method for increasing the tensile strength of connective tissue in a mammalian or avian species comprising administering to said mammalian or avian species a pharmaceutical composition containing an effective amount of a combination of prolactin and ascorbic acid or prolactin and an ascorbate as active ingredients therein.

* * * * *

UNITED STATES PATENT AND TRADEMARK OFFICE
CERTIFICATE OF CORRECTION

PATENT NO. : 5,162,303

DATED : November 10, 1992

INVENTOR(S) : Goodman

It is certified that error appears in the above-identified patent and that said Letters Patent is hereby corrected as shown below:

Column 13, lines 26 and 28, delete "3" and replace with --1--.

Column 14, lines 17 and 20, delete "17" and replace with --10--.

Signed and Sealed this

Second Day of November, 1993

Attest:

BRUCE LEHMAN

Attesting Officer

Commissioner of Patents and Trademarks